(12) United States Patent
Fridman et al.

(10) Patent No.: US 9,254,384 B2
(45) Date of Patent: Feb. 9, 2016

(54) INNER HAIR CELL STIMULATION MODEL FOR USE BY A COCHLEAR IMPLANT SYSTEM

(71) Applicant: Advanced Bionics AG, Staefa (CH)

(72) Inventors: Gene Y. Fridman, Baltimore, MD (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 68 days.

(21) Appl. No.: 14/085,925

(22) Filed: Nov. 21, 2013

(65) Prior Publication Data

US 2014/0081352 A1 Mar. 20, 2014

Related U.S. Application Data

(63) Continuation of application No. 12/414,262, filed on Mar. 30, 2009, now Pat. No. 8,615,302, which is a continuation of application No. 10/992,390, filed on Nov. 17, 2004, now Pat. No. 7,522,961.

(51) Int. Cl.
*A61N 1/36* (2006.01)

(52) U.S. Cl.
CPC .................. *A61N 1/36032* (2013.01)

(58) Field of Classification Search
CPC .................. A61N 1/36032; A61N 1/0541
USPC ...................... 607/55–57, 136–137
See application file for complete search history.

(56) References Cited

U.S. PATENT DOCUMENTS

| | | |
|---|---|---|
| 4,532,930 A | 8/1985 | Crosby et al. |
| 4,612,934 A | 9/1986 | Borkan |
| 4,819,647 A | 4/1989 | Byers et al. |
| 4,905,285 A | 2/1990 | Allen et al. |
| 5,749,912 A | 5/1998 | Zhang et al. |
| 5,991,663 A | 11/1999 | Irlicht et al. |
| 6,064,913 A | 5/2000 | Irlicht et al. |
| 6,078,838 A | 6/2000 | Rubinstein |
| 6,129,753 A | 10/2000 | Kuzma |
| 6,154,678 A | 11/2000 | Lauro |
| 6,198,971 B1 | 3/2001 | Leysieffer |
| 6,216,045 B1 | 4/2001 | Black et al. |
| 6,219,580 B1 | 4/2001 | Faltys et al. |
| 6,289,247 B1 | 9/2001 | Faltys et al. |
| 6,308,101 B1 | 10/2001 | Faltys et al. |
| 6,600,955 B1 | 7/2003 | Zierhofer |
| 6,700,982 B1 | 3/2004 | Geurts et al. |
| 6,728,578 B1 | 4/2004 | Voelkel |
| 6,745,155 B1 | 6/2004 | Andringa et al. |

(Continued)

*Primary Examiner* — Paula J Stice
(74) *Attorney, Agent, or Firm* — Blank Rome, LLP (57) ABSTRACT

The stimulation provided in the electrically stimulated cochlea is modulated in accordance with the amplitude of a received acoustic signal and the onset of a sound in a received acoustic signal to provide increased sound perception. An onset time that corresponds to the onset of a sound is detected in an acoustic signal associated with a frequency band. A forcing voltage and a transmitting factor are determined, wherein the forcing voltage and the transmitting factor are associated with the frequency band at the detected onset time. The acoustic signal is modulated as a function of the forcing voltage and the transmitting factor to generate an output signal. The generated output signal can be used to stimulate the cochlea. The modulation strategy can be used in conjunction with sound processing strategies that employ frequency modulation, amplitude modulation, or a combination of frequency and amplitude modulation.

12 Claims, 7 Drawing Sheets

(56) References Cited

U.S. PATENT DOCUMENTS

| | | |
|---|---|---|
| 6,775,389 B2 | 8/2004 | Harrison et al. |
| 6,778,858 B1 | 8/2004 | Peeters |
| 6,826,430 B2 | 11/2004 | Faltys et al. |
| 6,915,166 B1 | 7/2005 | Stecker et al. |
| 6,980,864 B2 | 12/2005 | Faltys et al. |
| 7,003,876 B2 | 2/2006 | Crawford et al. |
| 7,054,689 B1 | 5/2006 | Whitehurst et al. |
| 7,082,332 B2 | 7/2006 | Blamey et al. |
| 7,162,415 B2 | 1/2007 | Holzrichter et al. |
| 7,171,272 B2 | 1/2007 | Blamey et al. |
| 7,200,504 B1 | 4/2007 | Fister |
| 7,203,548 B2 | 4/2007 | Whitehurst et al. |
| 7,225,027 B2 | 5/2007 | Zeng et al. |
| 7,242,985 B1 | 7/2007 | Fridman et al. |
| 7,277,760 B1 | 10/2007 | Litvak et al. |
| 7,292,890 B2 | 11/2007 | Whitehurst et al. |
| 7,292,891 B2 | 11/2007 | Hartley et al. |
| 7,292,892 B2 | 11/2007 | Litvak et al. |
| 7,308,303 B2 | 12/2007 | Whitehurst et al. |
| 7,310,558 B2 | 12/2007 | Van Hoesel |
| 7,317,945 B2 | 1/2008 | Litvak et al. |
| 7,347,746 B1 | 3/2008 | He |
| 7,349,741 B2 | 3/2008 | Maltan et al. |
| 7,376,466 B2 | 5/2008 | He et al. |
| 7,426,445 B1 | 9/2008 | Fister |
| 7,444,180 B2 | 10/2008 | Kuzma et al. |
| 7,445,528 B1 | 11/2008 | Kuzma |
| 7,450,994 B1 | 11/2008 | Mishra et al. |
| 7,522,961 B2 | 4/2009 | Fridman et al. |
| 7,599,500 B1 | 10/2009 | Segel et al. |
| 7,627,383 B2 | 12/2009 | Haller et al. |
| 7,660,631 B2 | 2/2010 | Whitehurst et al. |
| 7,684,858 B2 | 3/2010 | He et al. |
| 7,702,385 B2 | 4/2010 | Moffitt et al. |
| 7,702,396 B2 | 4/2010 | Litvak et al. |
| 7,706,892 B2 | 4/2010 | Colvin et al. |
| 7,729,758 B2 | 6/2010 | Haller et al. |
| 7,729,775 B1 | 6/2010 | Saoji |
| 7,799,037 B1 | 9/2010 | He |
| 7,801,600 B1 | 9/2010 | Carbunaru |
| 7,801,602 B2 | 9/2010 | McClure et al. |
| 7,857,819 B2 | 12/2010 | Jaax et al. |
| 7,860,570 B2 | 12/2010 | Whitehurst |
| 7,864,968 B2 | 1/2011 | Kulkarni et al. |
| 7,899,539 B2 | 3/2011 | Whitehurst et al. |
| 7,920,915 B2 | 4/2011 | Mann et al. |
| 7,949,395 B2 | 5/2011 | Kuzma |
| 7,995,771 B1 | 8/2011 | Faltys |
| 8,027,733 B1 | 9/2011 | Fridman et al. |
| 8,165,696 B2 | 4/2012 | McClure et al. |
| 8,175,710 B2 | 5/2012 | He |
| 8,175,717 B2 | 5/2012 | Haller et al. |
| 8,452,412 B2 | 5/2013 | Ibrahim |
| 2002/0123775 A1 | 9/2002 | O'Loughlin et al. |
| 2004/0015205 A1 | 1/2004 | Whitehurst et al. |
| 2004/0082980 A1 | 4/2004 | Mouine et al. |
| 2004/0136556 A1 | 7/2004 | Litvak et al. |
| 2004/0230254 A1 | 11/2004 | Harrison et al. |
| 2005/0222644 A1 | 10/2005 | Killian et al. |
| 2005/0240229 A1 | 10/2005 | Whitehurst et al. |
| 2005/0267555 A1 | 12/2005 | Marnfeldt et al. |
| 2006/0100672 A1 | 5/2006 | Litvak |
| 2007/0049988 A1 | 3/2007 | Carbunaru et al. |
| 2007/0239227 A1 | 10/2007 | Fridman |
| 2007/0260292 A1 | 11/2007 | Faltys et al. |
| 2007/0293785 A1 | 12/2007 | Litvak |
| 2010/0292759 A1 | 11/2010 | Hahn et al. |
| 2010/0331913 A1 | 12/2010 | Mann |
| 2011/0040350 A1 | 2/2011 | Griffith |
| 2011/0077579 A1 | 3/2011 | Harrison |

SIMULTANEOUS ANALOG STIMULATION BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250–500 | 500–875 | 875–1150 | 1150–1450 | 1450–2000 | 2000–2600 | 2600–3800 | 3800–6800 |
| 7 CHANNELS | 250–500 | 500–875 | 875–1150 | 1150–1450 | 1450–2000 | 2000–2600 | 2600–6800 | |
| 6 CHANNELS | 250–500 | 500–875 | 875–1150 | 1150–1750 | 1750–2600 | 2600–6800 | | |
| 5 CHANNELS | 250–500 | 500–875 | 875–1450 | 1450–2600 | 2600–6800 | | | |
| 4 CHANNELS | 250–875 | 875–1450 | 1450–2600 | 2600–6800 | | | | |
| 3 CHANNELS | 250–875 | 875–2600 | 2600–6800 | | | | | |
| 2 CHANNELS | 350–700 | 2200–4400 | | | | | | |
| 1 CHANNEL | 250–6800 | | | | | | | |

— 310

CIS BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250–500 | 500–730 | 730–1015 | 1015–1450 | 1450–2000 | 2000–2600 | 2600–3800 | 3800–6800 |
| 7 CHANNELS | 250–500 | 500–730 | 730–1150 | 1150–1750 | 1750–2600 | 2600–3800 | 3800–6800 | |
| 6 CHANNELS | 250–580 | 580–875 | 875–1450 | 1450–2000 | 2000–3300 | 3300–6800 | | |
| 5 CHANNELS | 250–580 | 580–1015 | 1015–1750 | 1750–3300 | 3300–6800 | | | |
| 4 CHANNELS | 250–730 | 730–1450 | 1450–2600 | 2600–6800 | | | | |
| 3 CHANNELS | 250–875 | 875–2000 | 2000–6800 | | | | | |
| 2 CHANNELS | 350–700 | 2200–4400 | | | | | | |
| 1 CHANNEL | 250–6800 | | | | | | | |

INNER HAIR CELL STIMULATION MODEL FOR USE BY A COCHLEAR IMPLANT SYSTEM

CROSS REFERENCE TO RELATED APPLICATIONS

This application is a continuation of U.S. patent application Ser. No. 12/414,262, filed Mar. 30, 2009, which is a continuation of U.S. patent application Ser. No. 10/992,390, filed Nov. 17, 2004 (now U.S. Pat. No. 7,522,961). Priority is claimed to both applications, and both are incorporated herein by reference in their entireties.

TECHNICAL FIELD

The present disclosure relates to implantable neurostimulator devices and systems, for example, cochlear stimulation systems, and to sound processing strategies employed in conjunction with such systems.

BACKGROUND

Prior to the past several decades, scientists generally believed that it was impossible to restore hearing to the profoundly deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech.

The electrical stimulation is implemented through a prosthetic device, known as a cochlear implant, which is implanted in the inner ear to restore partial hearing to profoundly deaf patients. Such cochlear implants generally employ an electrode array that is inserted into the cochlear duct. One or more electrodes of the array selectively stimulate different auditory nerves at different places in the cochlea based on the pitch of a received sound signal.

Within the cochlea, there are two main cues that convey "pitch" (frequency) information to the patient. There are (1) the place or location of stimulation along the length of a cochlear duct and (2) the temporal structure of the stimulating waveform. Sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals. The stimulation signals provided to the electrodes model the received acoustic signal associated with a particular frequency band. However, the stimulation signals do not necessarily accurately represent the signals generated by nerves.

Figure 1:
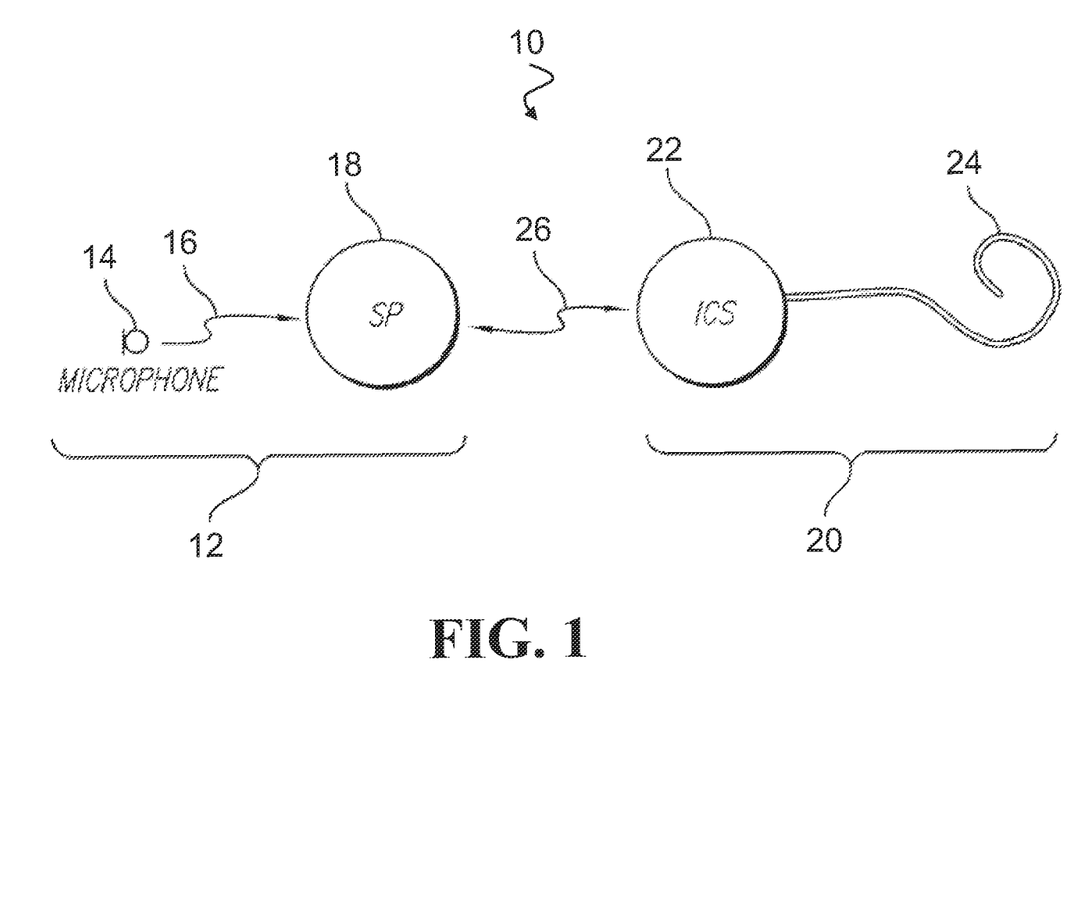
FIG. 1 is a block diagram of a cochlear stimulation system.

FIG. 1 presents a cochlear stimulation system 10 that includes a sound processor portion 12 and a cochlear stimulation portion 20. The sound processor portion 12 includes a microphone 14 and a sound processor 18. The microphone 14 can be connected directly to the sound processor 18. Alternatively, the microphone 14 can be coupled to the sound processor 18 through an appropriate communication link 16. The cochlear stimulation portion 20 includes an implantable cochlear stimulator 22 and an electrode array 24. The electrode array 24 is adapted to be inserted within the cochlea of a patient. The electrode array 24 includes a plurality of electrodes (not shown) that are distributed along the length of the array and are selectively connected to the implantable cochlear stimulator 22.

The electrode array 24 may be substantially as shown and described in U.S. Pat. Nos. 4,819,647 or 6,129,753, both patents incorporated herein by reference. Electronic circuitry within the implantable cochlear stimulator 22 allows a specified stimulation current to be applied to selected pairs or groups of the electrodes (not shown) included within the electrode array 24 in accordance with a specified stimulation pattern defined by the sound processor 18.

The sound processor 18 and the implantable cochlear stimulator 22 are electronically coupled through a suitable communication link 26. In an implementation, the microphone 14 and the sound processor 18 comprise an external portion of the cochlear stimulation system 10, and the implantable cochlear stimulator 22 and the electrode array 24 comprise an internal, or implanted, portion of the cochlear stimulation system 10. Thus, the communication link 26 is a transcutaneous (through the skin) link that allows power and control signals to be sent from the sound processor 18 to the implantable cochlear stimulator 22.

In another implementation, the implantable cochlear stimulator 22 can send information, such as data and status signals, to the sound processor 18 over the communication link 26. In order to facilitate bidirectional communication between the sound processor 18 and the implantable cochlear stimulator 22, the communication link 26 can include more than one channel. Additionally, interference can be reduced by transmitting information on a first channel using an amplitude-modulated carrier and transmitting information on a second channel using a frequency-modulated carrier.

In an implementation in which the implantable cochlear stimulator 22 and the electrode array 24 are implanted within the patient, and the microphone 14 and the sound processor 18 are carried externally (not implanted) by the patient, the communication link 26 can be realized though use of an antenna coil in the implantable cochlear stimulator 22 and an external antenna coil coupled to the sound processor 18. The external antenna coil can be positioned so that it is aligned with the implantable cochlear stimulator 22, allowing the coils to be inductively coupled to each other and thereby permitting power and information, e.g., a stimulation signal, to be transmitted from the sound processor 18 to the implantable cochlear stimulator 22. In another implementation, the sound processor 18 and the implantable cochlear stimulator 22 can both be implanted within the patient, and the communication link 26 can be a direct-wired connection or other suitable link as shown in U.S. Pat. No. 6,308,101, incorporated herein by reference.

In the cochlear stimulation system 10, the microphone 14 senses acoustic signals and converts the sensed acoustic signals to corresponding electrical signals. The electrical signals are sent to the sound processor 18 over an appropriate communication link 16, such as a circuit or bus. The sound processor 18 processes the electrical signals in accordance with a sound processing strategy and generates control signals used to control the implantable cochlear stimulator 22. Such control signals can specify or define the polarity, magnitude, location (which electrode pair or group is intended to receive the stimulation current), and timing (when the stimulation current is to be applied to the intended electrode pair or group) of the stimulation signal, such as a stimulation current, that is generated by the implantable cochlear stimulator 22.

It is common in the cochlear stimulator art to condition the magnitude and polarity of the stimulation current applied to the implanted electrodes of the electrode array 24 in accordance with a specified sound processing strategy. A sound processing strategy involves defining a pattern of stimulation waveforms that are applied as controlled electrical currents to the electrodes of an electrode array 24 implanted in a patient. Stimulation strategies can be implemented by modulating the amplitude of the stimulation signal or by modulating the frequency of the stimulation signal.

SUMMARY

The present inventors recognized the need to generate stimulation signals that account for the neural response of a healthy ear to received acoustic signals. Accordingly, the methods and apparatus described here implement techniques for enhancing sound as perceived through a cochlear implant. More specifically, the methods and apparatus described here implement techniques for using the inner hair cell model to emphasize the onsets of sound signals as perceived through a cochlear implant.

In general, in one aspect, the techniques can be implemented to include detecting an onset time corresponding to an onset of a sound in an acoustic signal associated with a frequency band; determining a forcing voltage and a transmitting factor, wherein the forcing voltage and the transmitting factor are associated with the frequency band at the detected onset time; and modulating the acoustic signal as a function of the forcing voltage and the transmitting factor to generate an output signal.

The techniques also can be implemented such that modulating the acoustic signal further comprises modulating the frequency of the acoustic signal. The techniques further can be implemented to include generating the output signal in accordance with a Frequency Modulated Stimulation (FMS) strategy such as that described in U.S. published patent application 2007/0239227, incorporated herein by reference. Additionally, the techniques can be implemented such that modulating the acoustic signal further comprises modulating the amplitude of the acoustic signal. Further, the techniques can be implemented to include generating the output signal in accordance with one of a Continuous Interleaved Stimulation (CIS) strategy, a Simultaneous Analog Stimulation (SAS) strategy, or a Hi-Resolution (HiRes) strategy.

The techniques also can be implemented such that modulating the acoustic signal further comprises modulating the frequency of the acoustic signal and the amplitude of the acoustic signal. Further, the techniques can be implemented such that modulating the acoustic signal further comprises modulating the acoustic signal as a function of a modulation constant. The techniques also can be implemented such that the generated output signal decays at a variable rate. The techniques further can be implemented such that the generated output signal comprises an acoustic signal. Additionally, the techniques can be implemented to include mapping the generated output signal to an electrical signal and applying the electrical signal to one or more electrode pairs of a cochlear implant.

In general, in another aspect, the techniques can be implemented to include a detector configured to detect an onset time corresponding to an onset of a sound in an acoustic signal associated with a frequency band and circuitry configured to determine a forcing voltage and a transmitting factor, wherein the forcing voltage and the transmitting factor are associated with the frequency band at the detected onset time, and to modulate the acoustic signal as a function of the forcing voltage and the transmitting factor to generate an output signal.

The techniques also can be implemented to include circuitry configured to modulate the frequency of the acoustic signal. Further, the techniques can be implemented to include circuitry configured to generate the output signal in accordance with a Frequency Modulated Stimulation strategy. Additionally, the techniques can be implemented to include circuitry configured to modulate the amplitude of the acoustic signal. Further still, the techniques can be implemented to include circuitry configured to generate an output signal in accordance with one of a Continuous Interleaved Stimulation strategy, a Simultaneous Analog Stimulation strategy, or a HiRes strategy.

The techniques also can be implemented to include circuitry configured to modulate the frequency of the acoustic signal and the amplitude of the acoustic signal. Further, the techniques can be implemented to include circuitry configured to modulate the acoustic signal as a function of a modulation constant. Additionally, the techniques can be implemented such that the generated output signal decays at a variable rate. The techniques further can be implemented such that the generated output signal comprises an acoustic signal. The techniques also can be implemented to include circuitry configured to map the generated output signal to an electrical signal and apply the electrical signal to one or more electrode pairs of a cochlear implant.

In general, in another aspect, the techniques can be implemented to include detecting a time corresponding to a sound in an acoustic signal; modeling a neural response to the sound in the acoustic signal at the detected time; and generating an output signal by modulating the acoustic signal as a function of the modeled neural response.

The techniques also can be implemented such that modeling a neural response comprises determining a forcing voltage as a function of an amplitude associated with the acoustic signal at the detected time and determining a transmitting factor as a function of a quantity of neurotransmitter available at the detected time. Additionally, the techniques can be implemented such that modulating the acoustic signal comprises modulating one or more of the frequency of the acoustic signal and the amplitude of the acoustic signal. Further, the techniques can be implemented such that modulating the acoustic signal comprises modulating the acoustic signal as a function of a modulation constant.

The techniques also can be implemented such that the generated output signal decays at a variable rate. Additionally, the techniques can be implemented such that the generated output signal comprises an acoustic signal. Further, the techniques can be implemented to include mapping the generated output signal to an electrical signal and applying the electrical signal to one or more electrode pairs of a cochlear implant.

The techniques described in this specification can be implemented to realize one or more of the following advantages. For example, the techniques can be implemented to emphasize the onsets of sound signals to account for the neural response of a healthy ear and thus improve sound clarity and speech recognition, especially under difficult listening conditions. The techniques also can be implemented to decrease the power consumption of a cochlear implant system implementing a sound processing strategy.

These general and specific aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION

Figure 2:
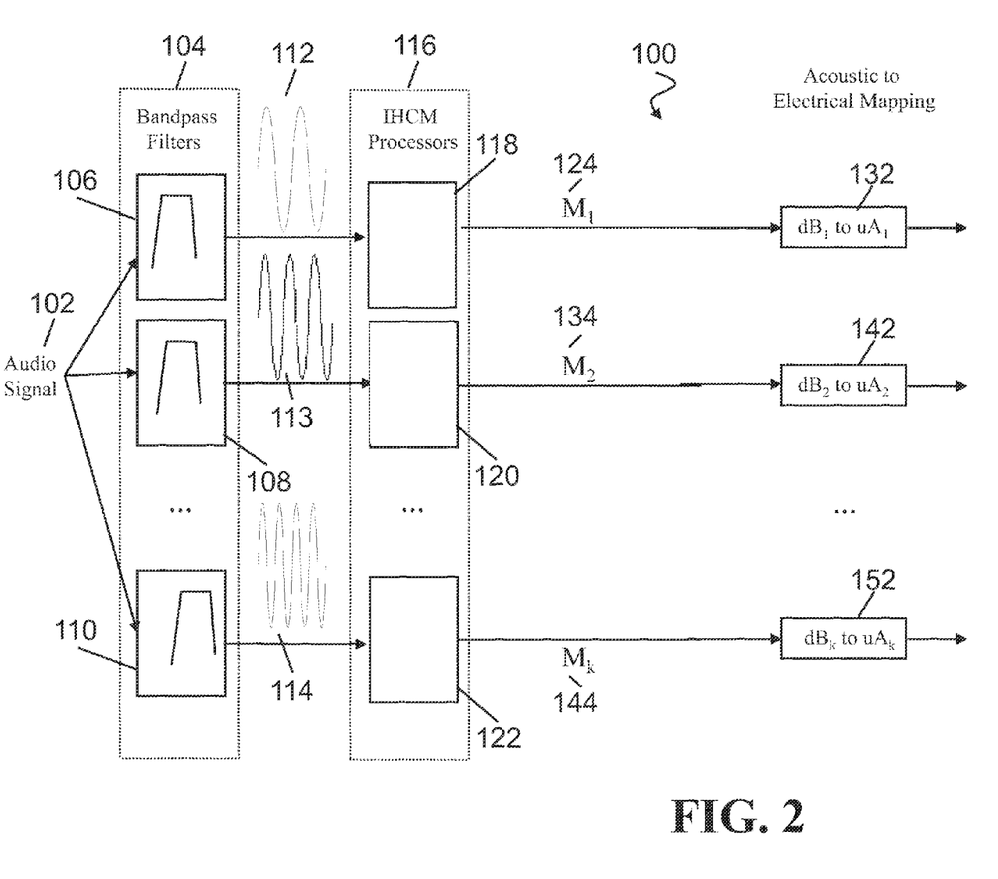
FIG. 2 is a functional block diagram of a sound processing system.

FIG. 2 presents a functional block diagram of a system arranged to implement a sound processing strategy. Such sound processing strategy can be implemented using any combination of circuitry and programmed instructions, including one or more of a programmable logic device, a field-programmable gate array, an application-specific integrated circuit, and a general purpose processor executing programmed instructions.

In the sound processing system 100, an audio signal 102 is provided as an input to a bank of bandpass filters 104, which separates the audio signal 102 into individual frequency bands or channels. For example, if the audio signal 102 is provided to a bank of K bandpass filters, then the audio signal 102 is separated into K individual frequency bands. In another implementation, different types and combinations of filters can be employed to separate the audio signal 102 into individual frequency bands, such as notch filters, high-pass filters, and low-pass filters.

As the audio signal 102 is provided to the bank of bandpass filters 104, individual bandpass filters output filtered signals. For example, the bank of bandpass filters 104 includes a bandpass filter 106 corresponding to a first frequency band, a bandpass filter 108 corresponding to a second frequency band, and a bandpass filter 110 corresponding to a $k_{th}$ frequency band. As the audio signal 102 is provided to the bank of bandpass filters 104, the bandpass filter 106 corresponding to the first frequency band outputs a filtered signal 112 associated with the first frequency band, the bandpass filter 108 corresponding to the second frequency band outputs a filtered signal 113 associated with the second frequency band, and the bandpass filter 110 corresponding to the $k_{th}$ frequency band outputs a filtered signal 114 associated with the $k_{th}$ frequency band. Thus, each filtered signal is associated with a frequency band that represents a subset of the audio signal 102.

Figure 3:
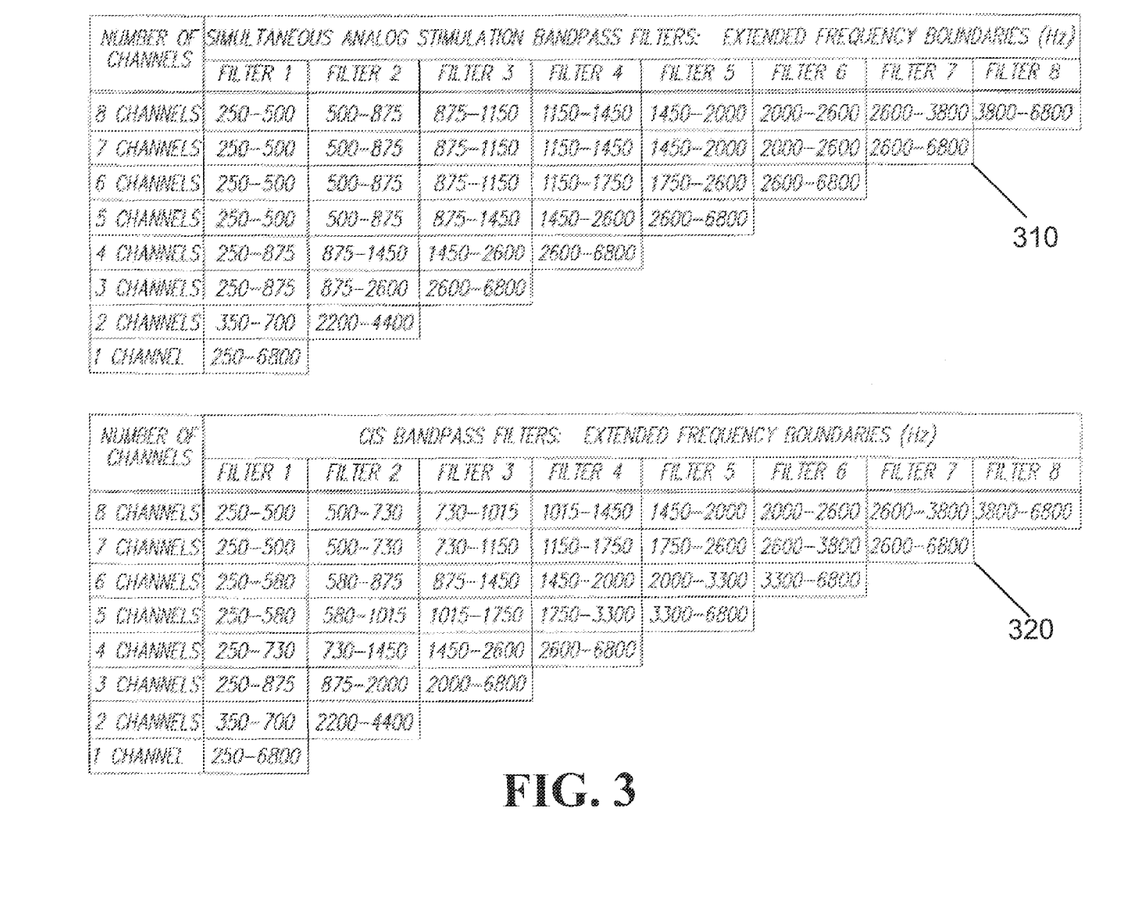
FIG. 3 presents exemplary frequency maps that can be used in conjunction with a sound processing strategy.

A sound processing strategy can be developed, which employs a plurality of specific frequency bands. The plurality of specific frequency bands corresponding to the particular sound processing strategy can be defined using a frequency map. FIG. 3 presents an example of a frequency map associated with the SAS strategy 310 and a frequency map associated with the CIS strategy 320. Other sound processing strategies, such as the FMS strategy, can be implemented using either of the frequency maps presented in FIG. 3, or by using alternative frequency maps. After the frequency map corresponding to a particular sound processing strategy has been defined, the bank of bandpass filters 104 can be configured to separate the audio signal 102 into frequency bands that correspond to the defined frequency map.

In another implementation, the audio signal 102 may undergo other processing before being provided as input to the bank of bandpass filters 104. For example, the audio signal 102 may originate as acoustic information sensed by a microphone, which is then converted into an electrical signal representing an audio signal. The electrical signal can further be converted to a digital signal in an analog-to-digital converter, and then be subjected to automatic gain control (AGC) processing using an AGC algorithm. The AGC algorithm serves to compress the dynamic range of the audio signals to provide a more consistent level of stimulus to the electrodes and to equalize the level between sound sources that are removed from the listener by differing distances.

The signals output from the bank of bandpass filters 104 are then provided to a bank of inner hair cell model (IHCM) processors 116. The firing rate of auditory nerve fibers increases with the amplitude of a received acoustic signal and is highest near the onset of a sound. Therefore, the IHCM processors included in the bank of IHCM processors 116 are configured to model the firing rate of auditory nerve fibers in a healthy ear. The bank of IHCM processors 116 includes an IHCM processor 118 corresponding to the first frequency band, an IHCM processor 120 corresponding to the second frequency band, and an IHCM processor 122 corresponding to the $k_{th}$ frequency band. The IHCM processors of the bank of IHCM processors 116 receive as input the filtered signals output from the corresponding bandpass filters in the bank of bandpass filters 104. For example, the IHCM processor 118 corresponding to the first frequency band receives as input the filtered signal 112 associated with the first frequency band from the bandpass filter 106 corresponding to the first frequency band. Similarly, the IHCM processors 120 and 122 corresponding to the second frequency band and the $k_{th}$ frequency band receive as input the filtered signals 113 and 114 associated with the second frequency band and the $k_{th}$ frequency band respectively.

The IHCM processors of the bank of IHCM processors 116 then transduce the received filtered signals to produce processed signals. Additionally, the IHCM processors determine a modulation factor $X_0$, as described below, and apply the modulation factor $X_0$ to the processed signals to produce modulated signals. For example, the IHCM processor 118 corresponding to the first frequency band transduces the received filtered signal 112 associated with the first frequency band to produce a processed signal. The IHCM processor 118 also determines a modulation factor $X_0$ associated with the first frequency band and applies the modulation factor $X_0$ to the processed signal to produce a modulated signal $M_1$ 124 associated with the first frequency band.

In an implementation, each IHCM processor of the bank of IHCM processors 116 includes an envelope detector, which receives as input the filtered signal output by the corresponding bandpass filter. The envelope detector included with the IHCM processor is configured to determine an envelope of the received filtered signal and to produce a processed signal, such as a representative envelope signal. For example, the filtered signal 112 associated with the first frequency band is provided as input to the envelope detector included with the IHCM processor 118 corresponding to the first frequency band, which determines the envelope of the filtered signal 112 and produces a processed signal. The IHCM processor 118 then produces a modulated signal $M_1$ 124 associated with the first frequency band using the processed signal and the modulation factor $X_0$. Each envelope detector can also include a rectifier, such as a half-wave rectifier or a full-wave rectifier, that rectifies the filtered signal output from the corresponding bandpass filter of the bank of bandpass filters 104 before the envelope of the filtered signal is determined.

Additionally, the envelope detectors included with the IHCM processors of the bank of IHCM processors 116 can comprise integrators that determine an average amplitude of a signal for a given interval. For example, upon receiving the filtered signal 112 associated with the first frequency band, the envelope detector included with the IHCM processor 118 corresponding to the first frequency band determines the envelope of the filtered signal 112 for an interval, such as a frame. At the end of the interval, the envelope detector produces a processed signal that represents the average amplitude of the filtered signal 112 associated with the first frequency band for that interval. As described above, the IHCM processor 118 corresponding to the first frequency band then produces a modulated signal $M_1$ 124 associated with the first frequency band using the processed signal and the modulation factor $X_0$. Each envelope detector can be further configured to set the average amplitude value of a received filtered signal to an initial state prior to the start of a new interval.

In another implementation, each IHCM processor of the bank of IHCM processors 116 includes a phase locking mechanism (PLM). In a healthy cochlea, the spiral ganglion cells located at the lower frequency end of the basilar membrane respond in phase with the vibration period of the basilar membrane. Similarly, the spiral ganglion cells located at the higher frequency end of the basilar membrane respond in phase at integer multiples of the vibration period of the basilar membrane. This response behavior is emulated using the PLM.

Each PLM generates pulse signals at integer multiples of the periods of the received filtered signal associated with the corresponding frequency band. The PLM processor determines the periods by monitoring the intervals between the positive-to-negative zero crossings of the received filtered signal. Each PLM processor can modulate the number of periods that are skipped between two consecutive pulses by the amplitude of the filtered signal associated with the frequency band. The number of periods $N_i$ to be skipped for a frequency band i having a center frequency Fc can be calculated using the linear approximation shown in equation 1.

$$N_i = \text{ceil}\left(\frac{M_i}{1/Fc_i}\right) = \text{ceil}(M_i * Fc_i) \tag{1}$$

As shown in equation 2, the parameter $M_i$ can be modulated between $M_{min}$ and $M_{max}$ milliseconds (ms) by the amplitude of the signal output from the bandpass filter associated with the frequency band i, $BPF_i$. In a healthy ear, the interval between spikes typically falls between $M_{min}=1$ and $M_{max}=3$ ms. The parameter $BPF_{i,max}$ represents the maximum output of the bandpass filter when the input is calibrated to a particular value, such as 65 decibel sound pressure level white noise.

$$M_i = \frac{M_{max} - M_{min}}{BPF_{i,max}} * BPF_i + M_{max} \tag{2}$$

The modulated signals output from the IHCM processors of the bank of IHCM processors 116 are converted to electrical signals using acoustic-to-electrical mappings associated with the corresponding frequency bands. Each of the resulting electrical signals is then applied to electrodes of a cochlear implant to provide a stimulation signal. For example, the modulated signal $M_1$ 124 associated with the IHCM processor 118 corresponding to the first frequency band is converted from an acoustic signal to an electrical signal using the acoustic-to-electrical mapping 132 associated with the first frequency band. Similarly, the modulated signals $M_2$ 134 and $M_k$ 144 are converted to electrical signals using the acoustic-to-electrical mappings 142 and 152 associated with the second frequency band and the $k_{th}$ frequency band respectively. The electrical signals output from the acoustic-to-electrical mappings are then provided as stimulation signals to the electrodes of a cochlear implant.

In another implementation, a signal generation queue can be employed to ensure that two or more stimulation signals are never delivered to the electrodes of a cochlear implant simultaneously. For example, the signal generation queue can monitor the modulated signals output from the bank of IHCM processors 116, such as the modulated signal $M_1$ 124 associated with the first frequency band and the modulated signal $M_k$ 144 associated with the $k_{th}$ frequency band. The signal generation queue can then control the output of stimulation signals associated with the modulated signals $M_1$ 124 and $M_k$ 144 in a temporally-separated, first-in-first-out manner. By preventing the simultaneous delivery of two or more stimulation signals, the unfavorable effects of electrical channel interaction can be minimized.

Figure 4:
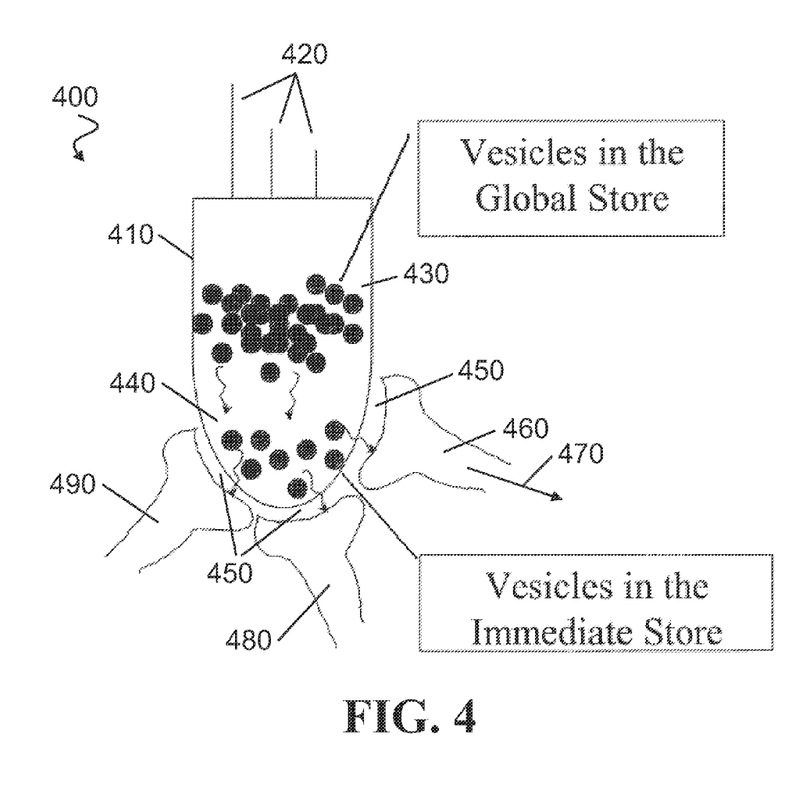
FIG. 4 presents a model of an inner hair cell.

FIG. 4 presents a model of an inner hair cell. A plurality of inner hair cells are arranged within the organ of Corti, which lies on the basilar membrane inside of the cochlea. Acoustic signals entering the cochlea cause the basilar membrane to vibrate, or deflect from a neutral position. In turn, the vibration of the basilar membrane creates mechanical stimulus that triggers one or more of the inner hair cells. The inner hair cells transduce the mechanical stimulus associated with the vibration of the basilar membrane into neural impulses, which are transmitted along the auditory nerve.

As demonstrated by the inner hair cell model 400, an individual inner hair cell 410 includes a plurality of hairs 420 that receive mechanical stimulus associated with the vibration of the basilar membrane. When one or more of the plurality of hairs 420 included in the inner hair cell are triggered by a received mechanical stimulus, the inner hair cell 410 releases neurotransmitter into the synaptic cleft 450 that lies between the inner hair cell 410 and one or more adjoining nerve fibers 460, 480, and 490. Each of the adjoining nerve fibers 460, 480, and 490 is associated with a nerve cell. The inner hair cell 410 can communicate with a plurality of nerve fibers 460, 480, and 490. However, each of the nerve fibers 460, 480, and 490 can only be triggered by an individual inner hair cell 410.

The inner hair cell 410 also includes a global store 430 and an immediate store 440. The global store 430 functions as a factory to produce the neurotransmitter that is released by the inner hair cell 410 in response to received stimulus. In the global store 430, small quantities of neurotransmitter are packaged into individual vesicles for storage. After production, the vesicles of neurotransmitter pass from the global store 430 to the immediate store 440 at a variable rate, depending on the relative concentrations of neurotransmitter in the global store 430 and the immediate store 440.

As described above, when one or more of the plurality of hairs 420 of the inner hair cell 410 are triggered by mechanical stimulus, the inner hair cell 410 releases the neurotransmitter stored in a number of vesicles in the immediate store 440 into the synaptic cleft 450. The number of vesicles in the immediate store 440 that may be used by the inner hair cell 410 to release neurotransmitter represents a transmitting factor, which influences whether an impulse can be triggered. As neurotransmitter is released into the synaptic cleft 450, the concentration of neurotransmitter in the proximity of one or more of the nerve fibers 460, 480, and 490 increases, which raises the probability that one or more of the nerve fibers 460, 480, and 490 will be triggered to generate an impulse 470 that will be transmitted to the auditory nerve.

When the immediate store 440 releases vesicles, the relative concentrations of neurotransmitter in the global store 430 and the immediate store 440 change and vesicles of neurotransmitter are transferred from the global store 430 to the immediate store 440. However, the rate at which the global store 430 can produce vesicles of neurotransmitter is limited. Therefore, once the inner hair cell 410 has released all of its stored vesicles, it can only continue to release vesicles at the rate at which they are received from the global store 430. The supply of vesicles in the immediate store 440 can only be replenished once the stimulus triggering the inner hair cell 410 has stopped. As such, the number of vesicles in the immediate store 440 at any point in time depends on several factors, including the interval of time that has passed since the immediate store 440 last released neurotransmitter in response to a received stimulus and the relative concentration of neurotransmitter remaining in the immediate store 440 after the previous release.

The number of vesicles released from the immediate store 440 depends upon the number of vesicles in the immediate store 440 at the time the mechanical stimulus is received and the perceived strength of the mechanical stimulus. The perceived strength of the mechanical stimulus is associated with the amplitude of the vibration of the basilar membrane at the location corresponding to the inner hair cell 410, which in turn is related to the amplitude of the received acoustic signal. Therefore, an inner hair cell 410 is most likely to release a large quantity of neurotransmitter, and thereby trigger a nerve fiber 460 to generate an impulse 470, when the amplitude of the received acoustic signal is high and the number of vesicles in the immediate store 440 of the inner hair cell 410 is large.

Figure 5:
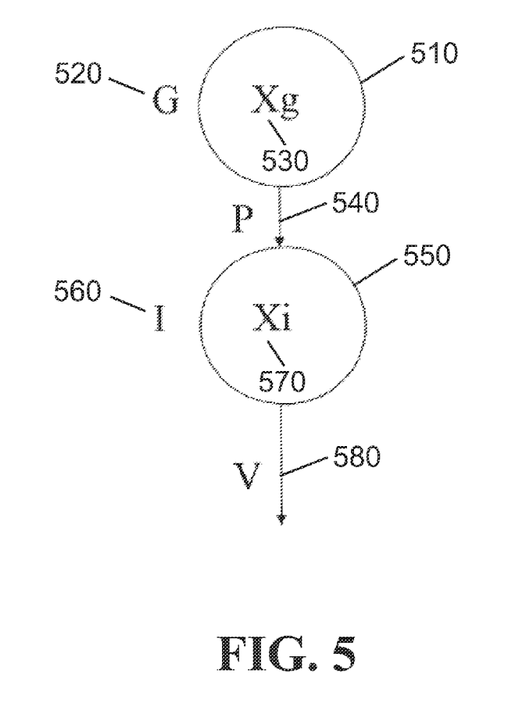
FIG. 5 presents a simplified model of an inner hair cell.

The inner hair cell model presented in FIG. 4 can be simplified as shown in FIG. 5, and the simplified model can be used to estimate the number of vesicles of neurotransmitter in the immediate store $X_i$ at a specific point in time. The global store 510 can be modeled using the volume of the global store G 520 and the number of vesicles in the global store $X_g$ 530. The density of vesicles in the global store 510 at a specific point in time can thus be determined by dividing the number of vesicles in the global store $X_g$ 530 by the volume of the global store G 520. Similarly, the immediate store 550 can be modeled using the volume of the immediate store I 560 and the number of vesicles in the immediate store $X_i$ 570. The density of vesicles in the immediate store 550 at a specific point in time can thus be determined by dividing the number of vesicles in the immediate store $X_i$ 570 by the volume of the immediate store I 560.

The number of vesicles that flow out of the immediate store 550 when a stimulus is received can be modeled using the density of vesicles in the immediate store and the voltage V forcing vesicle release 580 from the immediate store. The voltage V forcing vesicle release 580 corresponds to force the plurality of hairs 420 of the inner hair cell 410 perceive as a result of the vibration of the basilar membrane.

Additionally, the number of vesicles that flow from the global store 510 to the immediate store 550 can be modeled according to the relative densities of the global store 510 and the immediate store 550 in conjunction with a permeability constant 540. As vesicles are forced out of the immediate store 550 in accordance with the voltage V forcing vesicle release 580, the density of vesicles in the immediate store 550 decreases. Vesicles from the global store 510 then flow to the immediate store 550 in response to the change in the relative densities. The permeability constant 540 influences the rate at which the vesicles may be transferred.

The simplified model presented with reference to FIG. 5 can be used to determined the change in the number of vesicles in the immediate store 550 with respect to time, as shown in equation 3.

$$\frac{dX_i}{dt} = P \cdot \left(\frac{X_g}{G} - \frac{X_i}{I}\right) - (V \cdot X_i) \quad (3)$$

Using equation 3, it can be seen that the change in the number of vesicles in the immediate store $dX_i$ over time can be determined using the density of the vesicles in the global store $X_g/G$, the permeability constant P, the density of the vesicles in the immediate store $X_i/I$, the voltage V forcing vesicle release from the immediate store, and the number of vesicles in the immediate store $X_i$.

Further, the first order differential equation shown in equation 3 can be reduced to a non-linear difference equation, as shown in equation 4.

$$X_{i_n} = \eta - (\theta + V \cdot dt) X_{i_{n-1}} \quad (4)$$

In equation 4, the number of vesicles in the immediate store $X_i$ at a time n can be represented as the difference between $\eta$, a constant representing the density of vesicles in the global store multiplied by the permeability constant P, and the sum of $\theta$, a constant representing the density of vesicles in the immediate store multiplied by the permeability constant P, and the voltage V forcing vesicle release as a function of time, the sum multiplied by the number of vesicles in the immediate store $X_i$ at the preceding time interval n−1.

The number of vesicles in the immediate store $X_i$ at a given time n, as given by equation 4, can then be used to determine a modulation factor $X_0$. The modulation factor $X_0$ can be used to model the neural response to a perceived acoustic signal associated with a particular frequency band, and can be expressed mathematically as shown in equation 5.

$$X_0 = \gamma V X_{i_n} \quad (5)$$

In equation 5, modulation factor X0 is represented as the number of vesicles in the immediate store $X_i$ at a given time n, multiplied by the voltage V forcing vesicle release from the immediate store, and the modulation constant $\gamma$. The resulting modulation factor $X_0$ can be used to modulate the inter-pulse interval of the output of a frequency modulated sound processing strategy, such as the FMS strategy. By applying the modulation factor $X_0$ to the output of a frequency modulated sound processing strategy, the stimulation signal will better approximate the neural response of a healthy ear to a perceived acoustic signal.

In another implementation, the modulation factor $X_0$ can be used to modulate the amplitude of the output of an amplitude modulated sound processing strategy, such as the CIS, SAS, or HiRes strategies. Applying the modulation factor $X_0$ to the output of an amplitude modulated sound processing strategy also produces a stimulation signal that better approximates the neural response of a healthy ear to a perceived acoustic signal. In still another implementation, the modulation factor $X_0$ can be used to modulate the output of a sound processing strategy that employs both frequency modulation and amplitude modulation.

Figure 6:
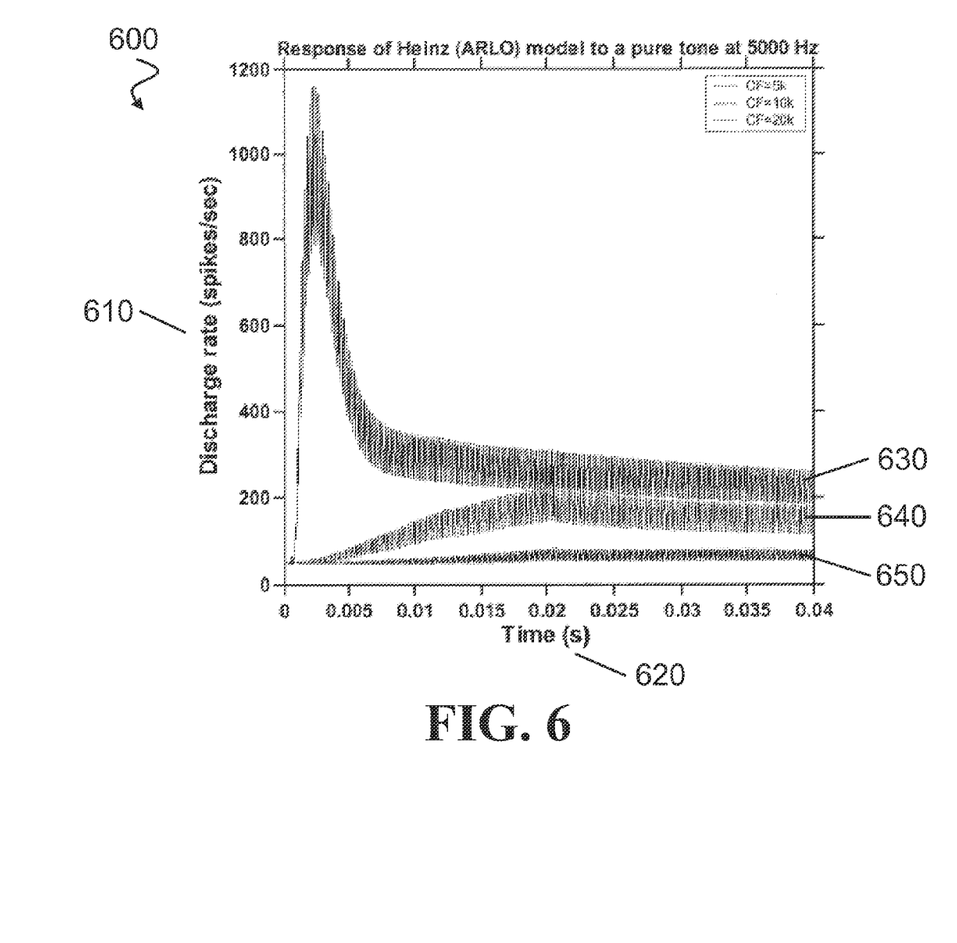
FIG. 6 presents a graphical depiction of neural response to a pure tone.

FIG. 6 presents a graphical depiction of neural response to a pure tone. The post stimulus time excitation histogram 600 plots the discharge rate 610, measured in spikes per second, over a period of time 620, measured in seconds, of the responses of models of three nerve fibers, where each of the nerve fibers is tuned to a different frequency band. The first nerve fiber is tuned to a first frequency band that has a center frequency of 5,000 Hz, the second nerve fiber is tuned to a second frequency band that has a center frequency of 10,000 Hz, and the third nerve fiber is tuned to a third frequency band that has a center frequency of 20,000 Hz.

The response to the introduction of a pure tone at 5,000 Hz is depicted by the discharge rate plots associated with each of the three nerve fibers. The first discharge rate plot 630 is associated with the first nerve fiber, the second discharge rate plot 640 is associated with the second nerve fiber, and the third discharge rate plot 650 is associated with the third nerve. As shown in the post stimulus time excitation histogram 600, discharges associated with each of the nerve fibers are seen following the introduction at time 0 of a pure tone at 5,000 Hz.

The discharge rate plots 640 and 650 associated with the second and third nerve fibers indicate that relatively few spikes occur in response to the introduction of the tone. However, the discharge rate plot 630 associated with the first nerve fiber tuned to the frequency band having a center frequency of 5,000 Hz indicates that a large number of spikes are generated in response to the tone. Further, the greatest number of spikes associated with the first nerve fiber are generated within the first 5 ms following onset of the tone. Therefore, incorporating the modulation factor $X_0$ into a sound processing strategy, as described above, results in a stimulation signal that corresponds more closely to the neural response of a healthy ear.

Figure 7:
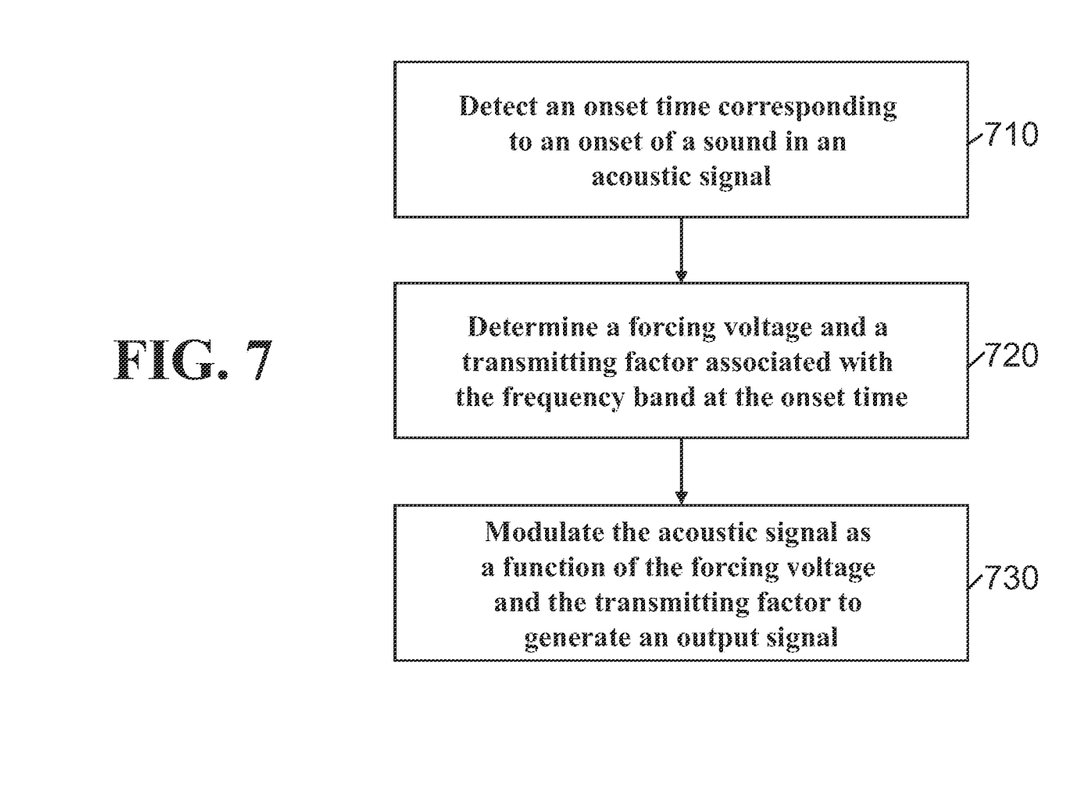
FIG. 7 is a flowchart of a method of stimulating a cochlea.

FIG. 7 describes a method of generating a cochlear stimulation signal using a strategy, such as the inner hair cell model, to emphasize the onsets of sound signals as perceived through a cochlear implant. In a first step 710, an onset time that corresponds to the onset of a sound in an acoustic signal is detected. The acoustic signal is associated with a frequency band. In a second step 720, a forcing voltage and a transmitting factor are determined. The forcing voltage and the transmitting factor are associated with the frequency band at the detected onset time. Once the forcing voltage and the transmitting factor have been determined, the third step is to modulate the acoustic signal as a function of the forcing voltage and the transmitting factor to generate an output signal.

A number of implementations have been disclosed herein. Nevertheless, it will be understood that various modifications may be made without departing from the spirit and scope of the claims. Accordingly, other implementations are within the scope of the following claims.

The invention claimed is:

1. An apparatus for generating a cochlear stimulation signal, the apparatus comprising:
 a plurality of bandpass filters each for receiving an audio signal and for producing a filtered signal comprising a band of frequencies;
 a plurality of processors, each processor for receiving one of the filtered signals and for producing a modulated signal, each processor comprising:
  an evelope detector, comprising an integrator,
 and wherein each processor is configured to:
  produce a processed signal representing the average amplitude of the received filtered signal,
  determine a modulation factor, and
  modulate an inter pulse interval of the processed signal by the modulation factor to produce the modulated signal.

2. The apparatus of claim 1, further comprising mapping circuitry for converting each modulated signal to an electrical signal.

3. The apparatus of claim 2, wherein the electrical signals are provided as stimulation signals to the electrodes of a cochlear implant.

4. The apparatus of claim 1, wherein the electrical signal is transmitted wirelessly.

5. The apparatus of claim 1, further comprising a microphone for providing the audio signal.

6. The apparatus of claim 1, wherein each processor includes an envelope detector configured to determine an envelope of the received filtered signal and to produce the processed signal.

7. The apparatus of claim 6, wherein the envelope detector comprises an integrator.

8. The apparatus of claim 1, wherein the band of frequencies comprises a center frequency and wherein each processor is further configured to generate pulses at integer multiples of periods of its received filtered signal, wherein the integer multiple comprises a function of the center frequency, the amplitude of the filtered signal, and a data indicative of a firing rate of auditory nerve fibers in a healthy ear.

9. The apparatus of claim 1, wherein each processer comprises a phase locking mechanism.

10. The apparatus of claim 9, wherein the phase locking mechanism emulates the phase relationship between ganglion cell response and basilar membrane vibration period in a healthy cochlea.

11. The apparatus of claim 10, wherein the data indicative of a firing rate of auditory nerve fibers in a healthy cochlea comprises a maximum and a minimum interval.

12. A method for generating a cochlear stimulation signal using the apparatus of claim 1, the method comprising:
 receiving an audio signal using the bandpass filters:
 producing a filtered signal from the received audio signal, using the bandpass filter, the filtered signal comprising a band of frequencies;
 generating a modulated signal from the filtered signal using the processors to produce a processed signal representing an average amplitude of the filtered signal, determining a modulation factor, and modulating an inter pulse interval of the processed signal by the modulaton factor to generated the modulated signal.

* * * * *